United States Patent
Zhou et al.

(10) Patent No.: US 11,148,125 B2
(45) Date of Patent: Oct. 19, 2021

(54) CATALYSTS FOR OLEFIN ISOMERIZATION

(71) Applicant: BRANDEIS UNIVERSITY, Waltham, MA (US)

(72) Inventors: Xiao Zhou, Waltham, MA (US); Yongwei Wu, Waltham, MA (US); Li Deng, Waltham, MA (US)

(73) Assignee: Brandeis University, Waltham, MA (US)

( * ) Notice: Subject to any disclaimer, the term of this patent is extended or adjusted under 35 U.S.C. 154(b) by 213 days.

(21) Appl. No.: 16/604,750

(22) PCT Filed: Apr. 10, 2018

(86) PCT No.: PCT/US2018/026906
§ 371 (c)(1),
(2) Date: Oct. 11, 2019

(87) PCT Pub. No.: WO2018/191270
PCT Pub. Date: Oct. 18, 2018

(65) Prior Publication Data
US 2020/0047169 A1 Feb. 13, 2020

Related U.S. Application Data

(60) Provisional application No. 62/485,549, filed on Apr. 14, 2017.

(51) Int. Cl.
*B01J 31/02* (2006.01)
*C07D 307/33* (2006.01)
*C07F 7/08* (2006.01)
*C07B 57/00* (2006.01)

(52) U.S. Cl.
CPC ....... *B01J 31/0244* (2013.01); *B01J 31/0202* (2013.01); *B01J 31/0204* (2013.01); *B01J 31/0239* (2013.01); *B01J 31/0271* (2013.01); *B01J 31/0274* (2013.01); *B01J 31/0275* (2013.01); *C07B 57/00* (2013.01); *C07D 307/33* (2013.01); *C07F 7/0812* (2013.01); *B01J 2231/52* (2013.01)

(58) Field of Classification Search
None
See application file for complete search history.

(56) References Cited

U.S. PATENT DOCUMENTS 9,469,633 B2   10/2016   Smejkal et al.

OTHER PUBLICATIONS

Provencher, B. A. et al. "Structural Study-Guided Development of Versatile Phase-Transfer Catalysts for Asymmetric Conjugate Additions of Cyanide" Angew. Chem. Int. Ed. 2011, 50, 10565-10569 (Year: 2011).*
Chinchilla, et al., "Polymer-Supported Cinchona Alkaloid-Derived Ammonium Salts as Recoverable Phase-Transfer Catalysts for the Asymmetric Synthesis of alpha-Amino Acids," Molecules, Apr. 30, 2004 (Apr. 30, 2004); vol. 9, p. 349-365, 352.
"Pubchem CID 101551383," Date Created: Dec. 18, 2015 (Dec. 18, 2015), Date Accessed: Jul. 30, 2018 (Jul. 30, 2018); p. 3, compound listed.
International Search Report and Written Opinion for corresponding PCT Patent Application No. PCT/US18/26906, dated Aug. 23, 2018 (14 pages).
Written opinion from the ISA for PCT/US2018/026906, dated Aug. 23, 2018, 5 pages.

* cited by examiner

*Primary Examiner* — Medhanit W Bahta
(74) *Attorney, Agent, or Firm* — Danielson Legal LLC

(57) ABSTRACT

Provided herein are cinchonium betaine catalysts and methods of promoting asymmetric butenolide isomerization reactions using the same.

2 Claims, No Drawings

CATALYSTS FOR OLEFIN ISOMERIZATION

CROSS REFERENCE TO RELATED APPLICATIONS

This patent application is the U.S. national phase application, pursuant to 35 U.S.C. §371, of PCT international application Ser. No.: PCT/US2018/026906, filed Apr. 10, 2018, designating the United States and published in English, which claims priority to and the benefit of U.S. Patent Application Ser. No. 62/485,549, filed Apr. 14, 2017, the entire contents of which are incorporated herein by reference.

STATEMENT OF RIGHTS TO INVENTIONS MADE UNDER FEDERALLY SPONSORED RESEARCH

This invention was made with government support under R01 GM061591 awarded by the National Institutes of Health. The government has certain rights in the invention.

BACKGROUND

Enzyme-mediated olefin isomerization via a proton transfer constitutes a common and important class of chemical reactions in biology. Isomerization of olefinic enzymes may substantially enhance catalytic rates. For example, $\Delta^5$-3 Ketosteroid isomerace (KSI) promotes an allylic rearrangement of β, γ- to α, β-unsaturated steroidal ketones involving intramolecular proton transfer via a dienolic intermediate resulting in a catalytic rate enhancement by a factor of 10. See Zhao Q, et al. Proc. Natl. Acad. Sci. U.S.A. 1996; 93(16):8220. However, KSI-catalyzed olefin isomerization does not generate a stereocenter. This catalyzed olefin isomerization is shown below and generally does not produce high values of enantiomeric excess.

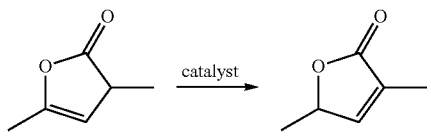

Similar isomerations are achieved via metal-mediated hydride transfer catalysis. Also, substrate-directed diastereoselective olefin isomerization with either achiral acids or bases have been applied in natural product synthesis. See Suenaga K, et al. Chem. Lett 2004; 33:918. Only a few examples of olefin isomerization by enantioselective proton transfer catalysis have been demonstrated. See Wu, Y, et al. J. Am. Chem. Soc. 2011; 133(32) 12458. Some of these examples are mediated by a bimetallic gadolinium complex. See Saga Y, et al. J. Am. Chem. Soc. 2010; 132: 7905. An example of such enantiomeric isomerization is illustrated below:

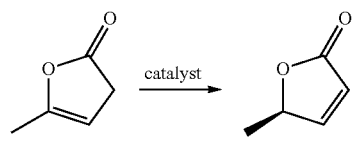

There is a need in the art to identify chiral organic catalysts that can be used to promote these highly enantioselective olefin isomerization reactions of general substrate scope in high yield and high enantiomeric excess. The presently disclosed compounds and methods meet this need.

SUMMARY

Provided herein are cinchonium betaine catalysts that can be used to promote butenolide isomerization in a highly chemoselective and enantioselective manner. In certain embodiments, the catalysts described herein allow for the asymmetric preparation of chiral amines.

Provided herein is a compound, or a salt, tautomer, enantiomer or diastereoisomer thereof useful as a catalyst of olefinic isomerization, having the structure of formula (I):

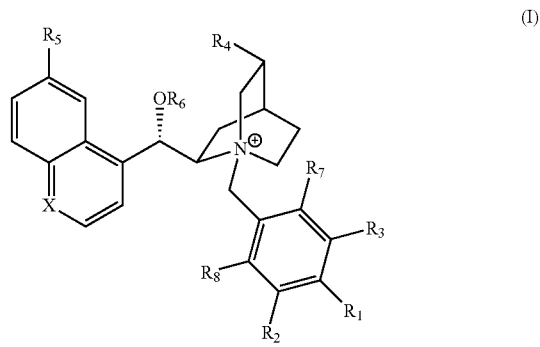

wherein X is selected from N and $N^+$—$O^-$;

$R_1$ is selected from hydrogen, $C_1$-$C_6$ alkoxy, $C_1$-$C_6$ alkyl siloxy (e.g., —OS(R)(R')(R'''), —OS(CH$_3$)$_3$, —OS(CH$_2$CH$_3$)$_3$, —OS(C(CH$_3$)$_3$)$_3$, etc.), or halogen;

$R_2$ and $R_3$ are independently selected from hydrogen, $C_1$-$C_6$ alkyl, or alkylsilyl (e.g., —S(R)(R')(R'''), —S(CH$_3$)$_3$, —S(CH$_2$CH$_3$)$_3$, —S[C(CH$_3$)$_3$]$_3$, etc.);

$R_4$ is $C_1$-$C_6$ alkyl or $C_2$-$C_7$ alkenyl;

$R_5$ is hydrogen, —OH, —O$^-$, or $C_1$-$C_6$ alkoxy (e.g., methoxy, ethoxy, propoxy, isopropoxy, butoxy, tert-butoxy, etc.);

$R_6$ is an optionally substituted $C_5$-$C_6$ heteroaryl, wherein each optional substituent is independently selected from aryl and halo, and said $C_5$-$C_6$ heteroaryl may comprise one or more (e.g. two, three, etc.) substituents in the carbon ring selected from O, N, and/or S; and $R_7$ and $R_8$ are independently selected from hydrogen, $C_1$-$C_6$ alkyl, or $C_1$-$C_6$ alkenyl; and $R_3$ and $R_7$ may together form a five or six membered optionally aromatic fused ring; and $R_2$ and $R_8$ may together form a five or six membered optionally aromatic fused ring. As used herein any R', R", or R''' may be independently selected at each occurrence from hydrogen or a $C_1$-$C_6$ hydrocarbon including methyl, ethyl, butyl, tert-butyl, phenyl, etc.) In some embodiments, $R_5$ is selected from —OH or —O$^-$ or alkoxy (e.g., methoxy, ethoxy, propoxy, isopropoxy, butoxy, tert butoxy, etc.). In some embodiments, $R_2$ and $R_3$ are the same functional group (e.g., both are phenyl, both are napthyl, both are trimethylsilyl, both are hydrogen, etc.). In some embodiments, $R_2$ and $R_3$ are each phenyl. In some embodiments, $R_2$ and $R_3$ are each napthyl. In some embodiments, $R_1$ is selected from methoxy, tert-butoxy and t-butyldimethylsiloxy (OTBS). In some embodiments, $R_4$ is —CH=CH$_2$. In some embodiments, $R_6$ has the structure of PYR:

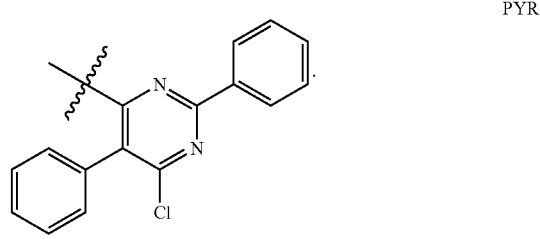 [SMILES: *c1nc(-c2ccccc2)nc(Cl)c1-c1ccccc1]

In some embodiments, the compound may form an ionic bond (e.g. a salt) with an anion. In some embodiments, the anion is a bromine anion.

Exemplary compounds of the invention are shown below in Table 1. In some embodiments, the compound may be any compound disclosed in Table 1.

TABLE 1

| Compound Number | Compound Name | Compound Structure |
|---|---|---|
| 1 | (1S,2R,4S,5R)-2-((S)-((6-chloro-2,5-diphenylpyrimidin-4-yl)oxy)(6-hydroxyquinolin-4-yl)methyl)-1-((2'-tertbutylsiloxyl-[1,1':3',1''-terphen]-5'-yl)methyl)-5-vinylquinuclidin-1-ium | 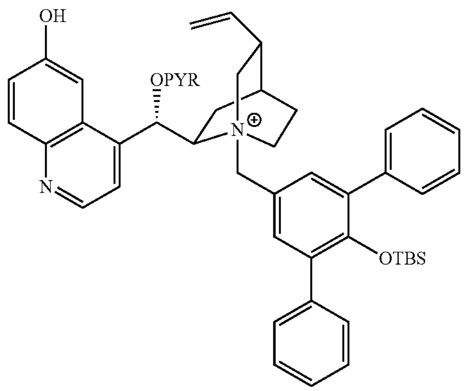 |
| 2 | (1S,2R,4S,5R)-2-((S)-((6-chloro-2,5-diphenylpyrimidin-4-yl)oxy)(6-hydroxyquinolin-4-yl)methyl)-1-((2'-methoxy-[1,1':3',1''-terphen]-5'-yl)methyl)-5-vinylquinuclidin-1-ium | 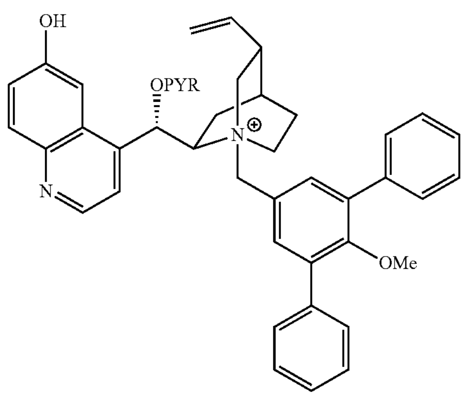 |
| 3 | (1S,2R,4S,5R)-2-((S)-((6-chloro-2,5-diphenylpyrimidin-4-yl)oxy)(6-hydroxyquinolin-4-yl)methyl)-1-((2'-tert-butoxy-[1,1':3',1''-terphen]-5'-yl)methyl)-5-vinylquinuclidin-1-ium | 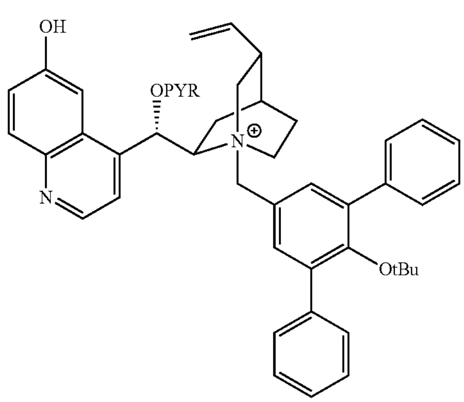 |

TABLE 1-continued

| Compound Number | Compound Name |
|---|---|
| 4 | (1S,2R,4S,5R)-2-((S)-((6-chloro-2,5-diphenylpyrimidin-4-yl)oxy)(6-hydroxyquinolin-4-yl)methyl)-1-((2'-tert-butoxy-3',4'-napth-2-yl-phenyl)methyl)-5-vinylquinuclidin-1-ium |
| 5 | (1S,2R,4S,5R)-2-((S)-((6-chloro-2,5-diphenylpyrimidin-4-yl)oxy)(6-hydroxyquinolin-4-yl)methyl)-1-((p-fluorophenylmethyl)-5-vinylquinuclidin-1-ium |
| 6 | (1S,2R,4S,5R)-2-((S)-((6-chloro-2,5-diphenylpyrimidin-4-yl)oxy)(6-hydroxyquinolin-4-yl)methyl)-1-benzyl)-5-vinylquinuclidin-1-ium |
| 7 | (1S,2R,4S,5R)-2-((S)-((6-chloro-2,5-diphenylpyrimidin-4-yl)oxy)(6-hydroxyquinolin-4-yl)methyl)-1-napth-1-yl)methyl)-5-vinylquinuclidin-1-ium |

TABLE 1-continued

| Compound Number | Compound Name | Compound Structure |
|---|---|---|
| 8 | (1S,2R,4S,5R)-2-((S)-((6-chloro-2,5-diphenylpyrimidin-4-yl)oxy)(6-hydroxyquinolin-4-yl)methyl)-1-(3,5 ditertbutyl, 4-methoxy-benzyl)-5-vinylquinuclidin-1-ium | 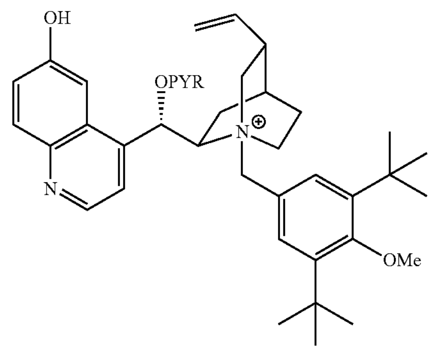 |
| 9 | (1S,2R,4S,5R)-2-((S)-((6-chloro-2,5-diphenylpyrimidin-4-yl)oxy)(quinolin-4-yl)methyl)-1-(3,5 ditertbutyl, 4-methoxy-benzyl)-5-vinylquinuclidin-1-ium | 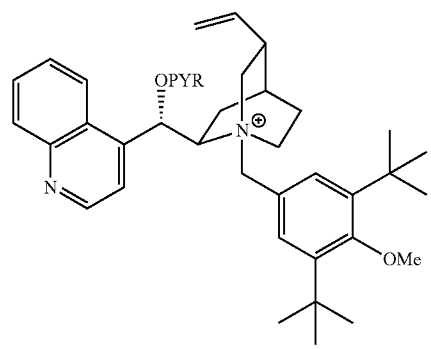 |
| 10 | (1S,2R,4S,5R)-2-(((6-chloro-2,5-diphenylpyrimidin-4-yl)oxy)(6-hydroxyquinolin-4-yl)methyl)-1-(3,5-di-tert-butylbenzyl)-5-vinylquinuclidin-1-ium | 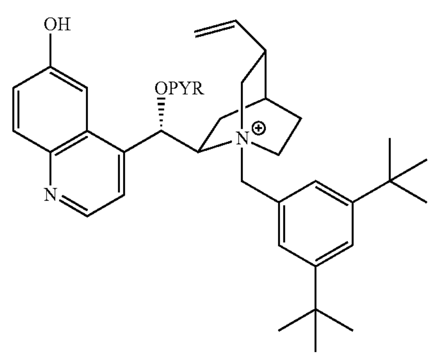 |
| 11 | 4-(((6-chloro-2,5-diphenylpyrimidin-4-yl)oxy)((1S,2R,4S,5S)-1-(3,5-di-tert-butylbenzyl)-5-ethylquinuclidin-1-ium-2-yl)methyl)-6-hydroxyquinoline 1-oxide | 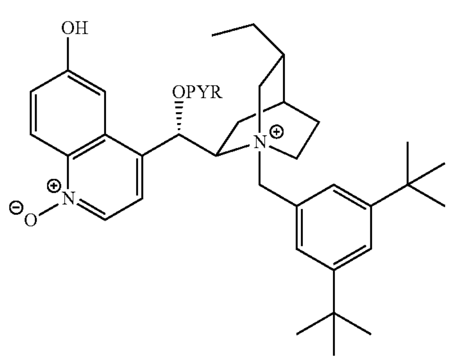 |

TABLE 1-continued

| Compound Number | Compound Name | Compound Structure |
|---|---|---|
| 12 | (1S,2R,4S,5R)-2-(((6-chloro-2,5-diphenylpyrimidin-4-yl)oxy)(6-hydroxyquinolin-4-yl)methyl)-1-(3,5-di-triethoxysilyl]benzyl)-5-vinylquinuclidin-1-ium | 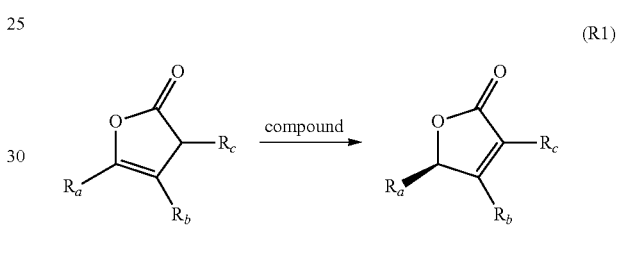 |

It will be understood that in the event of any inconsistency between a chemical name and formula, both compounds with the indicated chemical name and compounds with the indicated chemical structure will be considered as embraced by the invention. In some embodiments, the compounds are the diastereomers having the (1S,2R,4S,5R) at the stereocenter.

Provided herein is a method of promoting olefin isomerization that comprises contacting the olefin with at least one compound disclosed herein, wherein the olefin comprises formula

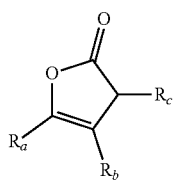

(II)

wherein $R_a$, $R_b$, $R_c$ and $R_d$ are independently selected from hydrogen, optionally substituted alkyl, optionally substituted aryl, optionally substituted cycloalkyl, and optionally substituted alkenyl, where each optional substituent is independently selected from hydroxy, alkyl, alkoxy, and halo; and $R_a$ and $R_b$ may together form a fused 5- or 6-membered ring. Contacting the olefin having the structure of formula (II) may afford a compound a compound having the structure of formula (III):

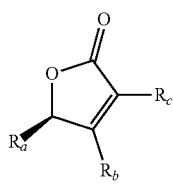

(III)

In some embodiments, $R_a$ is alkyl, such as methyl, ethyl, butyl, propyl, and n-butyl. In some embodiments, $R_a$ is substituted alkyl substituted with OH. In some embodiments, $R_a$ is phenyl, optionally substituted with methyl, methoxy or fluoro. In some embodiments, $R_b$ and $R_c$ are each hydrogen.

The isomerization reaction proceeds through reaction (R1) illustrated below.

(R1)

wherein the compound is any catalyst compound described herein.

In certain embodiments, the olefin (e.g. lactone, etc.) and the at least one compound are contacted in a system (e.g., an aqueous system) in the presence of a base. In some embodiments, the base is a hydroxide, such as NaOH or KOH. In other embodiments, the base can be a carbonate base, such as $Na_2CO_3$ or $K_2CO_3$. In other embodiments, the base can be a phosphate base, such as $K_3PO_4$. The amount of base in the system can be catalytic, such as about 5 mol % or about 10 mol % or about 15 mol % or about 20 mol %. In some embodiments, the system comprises a solvent. In preferred embodiments, the solvent may be selected from $CH_2Cl_2$, THF, toluene, EtOAc, $CH_3CN$, or $CHCl_3$. The solvent may be present in an amount of from about 0.001M-10M (e.g. 0.01M-1M, about 0.05 to about 0.5 M, etc.).

In some embodiments, the amount of the at least one compound in the system ranges from about 0.01 mol % to about 5 mol % with respect to the lactone, such as about 0.1 mol % to about 5 mol %, about 1 mol % to about 5 mol %, 0.1 mol % to about 0.1 mol %, such as about 0.05 mol % to about 1 mol %, such as about 0.1 mol % to about 0.5 mol %, or such as about 1.0 to about 3.0 mol %. In some embodiments, the amount of the at least one compound in the system is selected from about 0.01 mol %, about 0.02 mol %, about 0.05 mol %, about 0.08 mol %, about 0.1 mol %, about 0.2 mol %, about 0.3 mol %, about 0.4 mol %, about 0.5 mol %, about 1.0 mol %, about 2.0 mol %, about 3.0 mol % about 4.0 mol % and about 5.0 mol %.

DETAILED DESCRIPTION

Definitions

Unless defined otherwise, all technical and scientific terms used herein generally have the same meaning as commonly understood by one of ordinary skill in the art to which this disclosure pertains. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, such as ±5%, such as ±1%, and such as ±0.1% from the specified value, as such variations are appropriate to perform the disclosed methods.

As used herein, the term "alkyl", by itself or as part of another substituent means, unless otherwise stated, a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, iso-propyl, n-butyl, iso-butyl, sec-butyl, and tert-butyl. The term "$C_1$-$C_4$ n-alkyl" refers to straight chain hydrocarbon moieties that have 1, 2, 3, or 4 carbon atoms including methyl, ethyl, n-propyl, and n-butyl.

As used herein, the term "alkenyl" by itself or as part of another substituent means, unless otherwise stated, a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methyl-prop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like, and the higher homologs and isomers. A non-limiting functional group representing an alkene is exemplified by —$CH_2$—CH=$CH_2$.

As used herein, the term "alkoxy" by itself or as part of another substituent means, unless otherwise stated, an —O-alkyl group, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. In some embodiments, an alkoxy group can have one to six carbons denoted $C_1$-$C_3$. In some embodiments, $C_{1-4}$ alkoxy is an alkoxy group which encompasses both straight and branched chain alkyls of from 1 to 4 carbon atoms. In some aspects, the alkoxy group is a ($C_1$-$C_3$)alkoxy, such as, but not limited to, ethoxy and methoxy.

As used herein, the term "aryl" or "arene" employed alone or in combination with other terms means, unless otherwise stated, a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like.

As used herein, the term "cycloalkyl" by itself or as part of another substituent means, unless otherwise stated, a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_3$-$C_{13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_6$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_3$-$C_{13}$ carbocyclyl groups include the aforementioned $C_{3-8}$ carbocyclyl groups as well as octahydro-1H indenyl, decahydronaphthalenyl, spiro[4.5]decanyl and the like.

As used herein, the term "halo" or "halogen" employed alone or as part of another substituent means, unless otherwise stated, a fluorine, chlorine, bromine, or iodine atom, such as fluorine, chlorine, or bromine, further such as, fluorine or chlorine.

As used herein, the term "heterocycle", by itself or as part of another substituent means, unless otherwise stated, an unsubstituted or substituted, stable, mono- or multi-cyclic heterocyclic ring system that consists of carbon atoms and at least one heteroatom. A heterocycle refers to any 3- to 18-membered non-aromatic radical monocyclic or polycyclic moiety comprising at least one heteroatom selected from nitrogen, oxygen, phosphorous and sulfur. In some aspects, the heteroatom(s) are chosen from N, O, and S. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, aziridinyl, oxiranyl, and thioranyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2, 5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e] [1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

As used herein, the term "heteroaryl" or "heteroaromatic", by itself or as part of another substituent means, unless otherwise stated, a 5-18 membered monocyclic or polycyclic (e.g., bicyclic or tricyclic) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms.

For example, an N-containing "heteroaryl" or "heteroaromatic" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b] [1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo [h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d] pyridazinyl, 5,6,7,8,9,10 hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5]thieno [2,3-d]pyrimdinyl, 6,7,8,9-tetrahydro-5H-cyclohepta[4,5]thieno [2,3-d]pyrimidinyl, 5,6,7, 8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl).

Further examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. The aforementioned listings of heterocyclyl and heteroaryl moieties are intended to be representative and not limiting.

As used herein, the term "isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol  which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)- . The present chemical entities (e.g. catalysts, reactants, products, intermediates, lactones, olefins, etc.), and methods are meant to include all such possible isomers, including racemic mixtures, optically substantially pure forms and intermediate mixtures, unless the stereochemistry is shown. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. Some compositions described herein contain an enantiomeric excess of at least about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has a —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, Enantiomers, Racemates and Resolutions (Jacques, Ed., Wiley Interscience, New York, 1981); Wilen et al., Tetrahedron 33:2725 (1977); Stereochemistry of Carbon Compounds (E. L. Eliel, Ed., McGraw-Hill, N Y, 1962); and Tables of Resolving Agents and Optical Resolutions p. 268 (E. L. ElM, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, substitution with heavier isotopes such as deuterium affords greater stability (for example, increased half-life or reduced loading requirements). Isotopically-labeled compounds are prepared by any suitable method or by processes using an appropriate isotopically-labeled reagent in place of the non-labeled reagent otherwise employed.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated herein, including inorganic acids, organic acids, inorganic bases, organic bases, solvates, hydrates, or clathrates thereof. As used herein, the term "salt" embraces addition salts of free acids or free bases that are compounds useful in the methods described herein. In some cases, undesired salts may nonetheless possess properties such as high crystallinity, which may have utility in the practice of the methods described herein, such as, for example, utility in process of synthesis or purification of compounds described herein.

Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid.

Suitable base addition salts of disclosed compounds include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl-ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

A "substituted" hydrocarbon may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In some embodiments, a heteroatom or group may substitute a carbon. In some embodiments, a heteratom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo", replacing a hydrogen in the backbone or chain, etc.).

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo, $C_{1-12}$ straight chain or branched chain alkyl, $C_{2-12}$ alkenyl, $C_{2-12}$ alkynyl, $C_{3-12}$ cycloalkyl, $C_{6-12}$ aryl, C3-12 heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. Further, as used herein, the phrase "optionally substituted" means unsubstituted (e.g., substituted with an H) or substituted. As used herein, the term "substituted" means that a hydrogen atom is removed and replaced by a substituent (e.g., a common substituent). It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable.

For aryl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, such as straight.

Throughout this disclosure, various aspects of the disclosure may be presented in a range format. It should be understood that the description in range format is merely for convenience and brevity and should not be construed as an inflexible limitation on the scope of the present claims. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

Compounds and Methods

Provided herein are cinchonium betaine catalysts that can be used to promote olefin isomerization in a highly chemoselective and enantioselective manner. In certain embodiments, the catalysts described herein allow for the asymmetric preparation of chiral olefins. The present disclosure further includes compositions comprising one or more of the catalysts described herein, and methods of preparing certain organic compounds using these catalysts.

The present disclosure describes the discovery and development of chiral phase-transfer catalysts that promote highly efficient olefin isomerizations. Modified cinchona alkaloids, such as the quinidine-derived (QD) catalyst compound 1, can promote a highly enantioselective isomerization of various olefins. The reaction can be carried out in high yield with as little as about 0.01 mole percent catalyst, although in some embodiments, the catalyst is present in an amount greater than about 0.1 mol %, about 1.0 mol %, about 1.5 mol %, about 1.75 mol %, or about 2.0 mol %. These isomerization reactions provide a practical and efficient approach to chiral olefinic lactones (e.g., compounds having the structure of formula (III), etc.).

In certain embodiments, the olefin and the at least one compound are contacted in a non-aqueous system in the presence of a base. In some embodiments, the base is a hydroxide, such as NaOH or KOH. In other embodiments, the base can be a carbonate base, such as $Na_2CO_3$ or $K_2CO_3$. The amount of base in the system can be catalytic, such as about 10 mol %, about 15 mol % or about 20 mol %.

In some embodiments, the amount of the at least one compound in the system (e.g., the reaction system) ranges from about 0.01 mol % to about 5 mol % with respect to the lactone, such as about 0.01 mol % to about 0.1 mol %, such as about 0.05 mol % to about 1 mol %, such as about 0.1 mol % to about 0.5 mol %. In some embodiments, the amount of the at least one compound in the system is selected from about 0.01 mol %, about 0.02 mol %, about 0.05 mol %, about 0.08 mol %, about 0.1 mol %, about 0.2 mol %, about 0.3 mol %, about 0.4 mol %, and about 0.5 mol %.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and methods, and are not intended to limit the scope of what the inventor(s) regard(s) as the invention.

EXAMPLES

The compounds can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations,* 2d. Ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}F$ NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

The following Examples are provided for the purpose of illustration only, and the disclosure is not limited to these Examples, but rather encompasses all variations that are evident as a result of the teachings provided herein.

Example 1: Optimization of the Isomerization Reaction System

Isomerization reactions of were performed in various solvents to determine the solvent which providing most enantiomerically pure products, in order to determine the most effective reaction system to carry out the isomerization reaction in. The isomerization reactions and parameters of the screen for the reaction system solvent isomerization of compound 1A to 1B are described below:

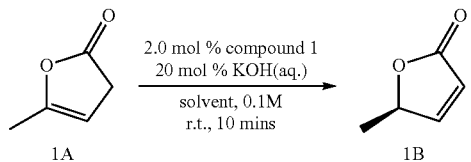

Table 2 shows the results of each reaction performed with various solvents.

TABLE 2

| solvent | conv. (%) | ee (%) |
|---|---|---|
| CH$_2$Cl$_2$ | 70 | 70 |
| THF | 73 | 59 |
| Toluene | 19 | 67 |
| EtOAc | 64 | 73 |
| CH$_3$CN | 18 | 64 |
| CHCl$_3$ | 52 | 77 |

As can be seen in Table 2, using CHCl$_3$ as a solvent produced the largest enantiomeric excess of compound 1B.

The isomerization reactions and parameters of the screen for the reaction system solvent isomerization of compound 1A to 1B are described below:

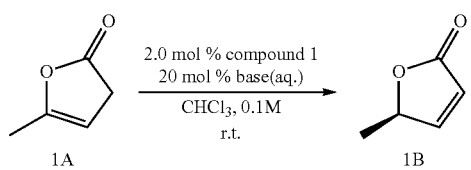

Table 3 shows the results of each reaction performed with various bases and reaction times.

TABLE 3

| base | t (min) | conv. (%) | ee (%) |
|---|---|---|---|
| 50% KOH | 10 | 52 | 77 |
| 33.3% K$_2$CO$_3$ | 10 | 3.3 | — |
|  | 60 | 6.8 | 72 |
| 50% K$_3$PO$_4$ | 10 | 6 | 76 |
|  | 60 | 13 | 76 |

The isomerization reaction parameters time ("t") and temperature ("T") as well as the catalysts ("cat.") compounds 1-12 were varied to optimize the reaction system by determining the amount of compound 1A converted to compound 1B (conv. (%)) and the enantiomeric excess. Reaction optimization parameters are shown below.

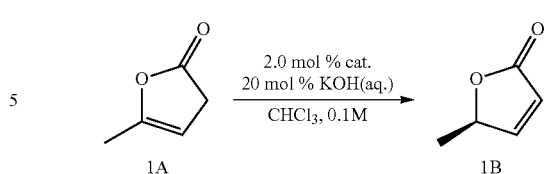

Table 4 illustrates the results of the reaction optimization.

TABLE 4

| Rxn. No. | cat. | T (° C.) | t | conv. (%) | ee (%) |
|---|---|---|---|---|---|
| 1 | comp. 1 | r.t. | 10 min | 52 | 77 |
| 2 | comp. 2 | r.t. | 10 min | 55 | 76 |
| 3 | comp. 3 | r.t. | 10 min | 52 | 76 |
| 4 | comp. 4 | r.t. | 10 min | 47 | 78 |
| 5 | comp. 5 | r.t. | 10 min | 54 | 80 |
| 6 | comp. 6 | r.t. | 10 min | 45 | 82 |
| 7 | comp. 7 | r.t. | 10 min | 58 | 84 |
| 8 | comp. 7 | 0 | 1 h | 50 | 89 |
|  |  |  | 5 h | 54 | 89 |
|  |  |  | 24 h | 55 | 89 |
| 9 | comp. 7 | -20 | 1 h | 9 | 87 |
|  |  |  | 5 h | 19 | 91 |
|  |  |  | 24 h | 29 | 92 |
| 10 | comp. 8 | r.t. | 10 min | 71 | 78 |
| 11 | comp. 8 | 0 | 1 h | 48 | 91 |
|  |  |  | 5 h | 74 | 88 |
|  |  |  | 24 h | 78 | 87 |
| 12 | comp. 8 | -20 | 1 h | 12 | 89 |
|  |  |  | 5 h | 25 | 91 |
|  |  |  | 24 h | 47 | 92 |
| 13 | comp. 9 | r.t. | 10 min | 1 | 0 |
|  |  |  | 1 h | 2 | 0 |
| 14 | comp. 10 | r.t. | 10 min | 69 | 81 |
| 15 | comp. 10 | 0 | 1 h | 17 | 90 |
|  |  |  | 5 h | 54 | 91 |
|  |  |  | 24 h | 60 | 91 |
| 16 | comp. 11 | r.t. | 10 min | 44 | 87 |
| 17 | comp. 11 | 0 | 5 h | 18 | 90 |
|  |  |  | 24 h | 18 | 89 |
| 18 | comp. 12 | r.t. | 10 min | 61 | 88 |
| 19 | comp. 12 | 0 | 5 h | 75 | 91 |
|  |  |  | 24 h | 76 | 90 |
| 20 | — | r.t. | 10 min | 1 | 0 |
|  |  |  | 1 h | 2 | 0 |

These studies demonstrate that lactones can be converted in a highly enantioselective manner into enantiomers of the corresponding optically lactone. With an accessible operational protocol and low catalyst loading, the transformations disclosed herein also provide a practical method for organic synthesis.

The disclosures of each and every patent, patent application, and publication cited herein are hereby incorporated herein by reference in their entirety.

While the disclosure has referenced specific embodiments, it is apparent that other embodiments and variations may be devised by others skilled in the art without departing from the true spirit and scope of the invention. The appended claims are intended to be construed to include all such embodiments and equivalent variations.

What is claimed:

1. A compound, or a salt tautomer, enantiomer or diastereoisomer thereof, of formula (I):

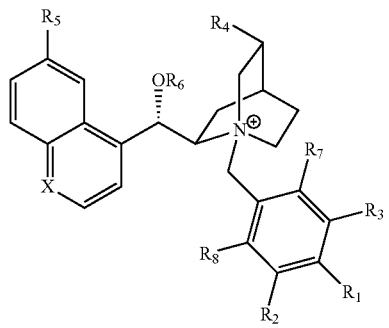

wherein X is N,
R1 is hydrogen;

R2 and R3 are independently selected from the group consisting of hydrogen and C1-C6 alkyl;

R4 is C1 alkyl;

R5 is —OH;

R6 is an optionally substituted C5 heteroaryl, wherein each optional substituent is independently selected from the group consisting of aryl and halo, and said C5 heteroaryl may comprise one or more substituents in the carbon ring, wherein the one or more substituents in the carbon ring are; and R7 and R8 are hydrogen.

2. The compound according to claim 1, wherein R2 and R3 are the same functional group.

* * * * *